United States Patent
Birgmann et al.

(10) Patent No.: US 9,227,235 B2
(45) Date of Patent: Jan. 5, 2016

(54) METHOD FOR PRODUCING A SMALL THIN-WALLED TUBE FROM A MAGNESIUM ALLOY

(75) Inventors: Alois Birgmann, Moosdorf (AT); Martin Brandecker, St. Peter (AT); Maria Kuehlein, Stubenberg (DE); Thomas Waltenberger, Braunau am Inn (AT)

(73) Assignee: LKR LEICHTMETALLKOMPE-TENZZENTRUM RANSHOFEN GMBH, Ranshofen (AT)

( * ) Notice: Subject to any disclaimer, the term of this patent is extended or adjusted under 35 U.S.C. 154(b) by 1017 days.

(21) Appl. No.: 13/321,427

(22) PCT Filed: May 19, 2010

(86) PCT No.: PCT/AT2010/000171
§ 371 (c)(1),
(2), (4) Date: Feb. 3, 2012

(87) PCT Pub. No.: WO2010/132910
PCT Pub. Date: Nov. 25, 2010

(65) Prior Publication Data
US 2012/0125070 A1    May 24, 2012

(30) Foreign Application Priority Data
May 19, 2009 (AT) .................................. A 780/2009

(51) Int. Cl.
*B21D 22/00* (2006.01)
*B21C 1/00* (2006.01)
(Continued)

(52) U.S. Cl.
CPC . *B21C 1/003* (2013.01); *B21C 1/24* (2013.01); *B21C 1/26* (2013.01); *B21C 3/04* (2013.01);
(Continued)

(58) Field of Classification Search
CPC ............ B21C 23/18; B21C 1/24; B21C 1/26; B21C 37/30; B21C 1/003; B21C 3/04; B21C 3/16; B21C 9/00; B21D 22/00; A61F 2/82; A61F 2210/0004; B21G 1/08

USPC ............................................. 72/267; 623/1.38
See application file for complete search history.

(56) References Cited

U.S. PATENT DOCUMENTS 1,802,785 A * 4/1931 Singer ............................. 72/266
1,982,677 A * 12/1934 Littler ............................. 72/362
(Continued)

FOREIGN PATENT DOCUMENTS

CN    1403225    3/2003
CN    1792381    6/2006
(Continued)

OTHER PUBLICATIONS

Wu, "Study of the Forming Process of the Minor Diameter Thin Wall Magnesium Alloy Tubes," *Engineering Technology*, No. 2, Series 1, pp. 6 and 27-36 (2009).
(Continued)

*Primary Examiner* — David B Jones
(74) *Attorney, Agent, or Firm* — Greenblum & Bernstein, P.L.C.

(57) ABSTRACT

The invention relates to a method for producing a small thin-walled tube for a medical application or for a medical product, in particular for a stent, wherein a blank of an in particular bioresorbable magnesium alloy is deformed to produce a small tube, after which the small tube is used for medical purposes or from which the medical product, such as a stent, can be made. In order to be able to produce the small tube in one step and with high precision, it is provided according to the invention that a male die (2) with a base body (3) and a mandrel (4) tapered relative to the base body (3) and the blank is provided with a blind hole or an opening, wherein a diameter of the blind hole or the opening of the blank is equal to or greater than an outer diameter of the mandrel (4), after which the blank with inserted mandrel (4) with the male die (2) is pressed forwards at least in part through a female die (5) with a receiving region (6) and a contouring region (7), wherein the contouring region (7) has a free diameter, which is larger than the outer diameter of the mandrel (4), but smaller than an outer diameter of the blank, in order to form the small tube.

14 Claims, 4 Drawing Sheets

Figure 4:
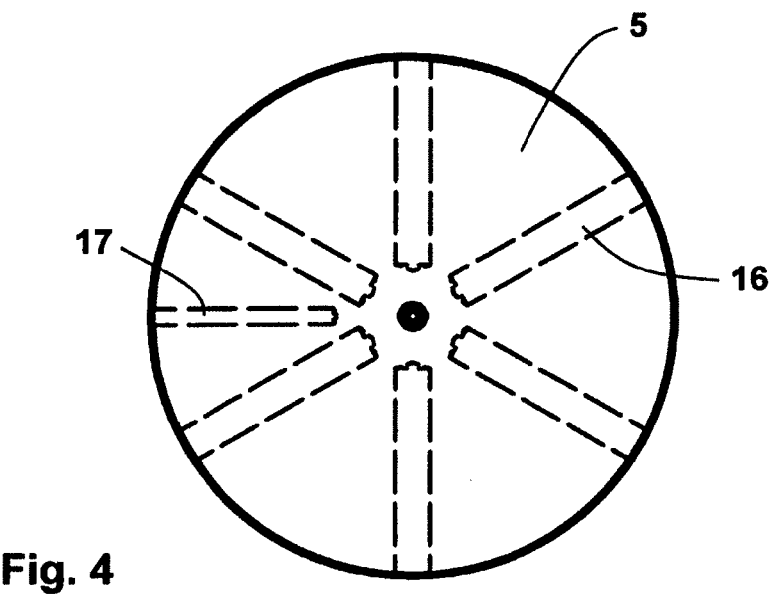

(51) Int. Cl.
    B21C 23/18    (2006.01)
    B21C 1/24     (2006.01)
    B21C 37/30    (2006.01)
    B21C 1/26     (2006.01)
    B21C 3/04     (2006.01)
    B21C 3/16     (2006.01)
    B21C 9/00     (2006.01)
    B21G 1/08     (2006.01)
    A61F 2/82     (2013.01)

(52) U.S. Cl.
    CPC ... B21C 3/16 (2013.01); B21C 9/00 (2013.01);
        B21C 23/18 (2013.01); B21C 37/30 (2013.01);
        B21D 22/00 (2013.01); B21G 1/08 (2013.01);
        *A61F 2/82* (2013.01); *A61F 2210/0004*
        (2013.01)

(56) References Cited

U.S. PATENT DOCUMENTS

| | | | | |
|---|---|---|---|---|
| 2,024,186 A * | 12/1935 | Rober | | 72/349 |
| 2,950,816 A | 8/1960 | Arenz | | |
| 3,394,578 A * | 7/1968 | Biginelli | | 72/254 |
| 3,552,173 A * | 1/1971 | Biginelli | | 72/257 |
| 3,851,516 A * | 12/1974 | Garner et al. | | 72/256 |
| 3,408,846 A1 | 11/2005 | Schofield | | |
| 8,202,477 B2 * | 6/2012 | Papirov et al. | | 420/402 |
| 2007/0077163 A1 | 4/2007 | Furst et al. | | |
| 2009/0056405 A1 * | 3/2009 | Uan et al. | | 72/368 |
| 2013/0218265 A1 * | 8/2013 | Becher et al. | | 623/1.46 |

FOREIGN PATENT DOCUMENTS

| | | |
|---|---|---|
| CN | 101015841 | 8/2007 |
| CN | 101085377 | 12/2007 |
| CN | 101549361 | 10/2009 |
| CN | 101549362 | 10/2009 |
| DE | 20 57 865 | 6/1971 |
| EP | 1 840 235 | 10/2007 |
| WO | 97/03769 | 2/1997 |

OTHER PUBLICATIONS

Chinese Office action conducted in counterpart Chinese Appln. No. 201080021868.X (Aug. 19, 2013) (w/ English language translation).
Japan Office Action conducted in counterpart Japan Appln. No. 2012-511089 (Nov. 26, 2013) (w/ partial English language translation).
European Office Action conducted in counterpart European Appln. No. 10 721 621.0-1702 (Dec. 23, 2014) (w/ English translation).

* cited by examiner

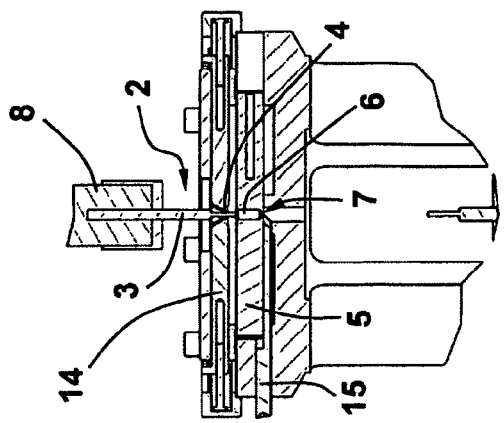
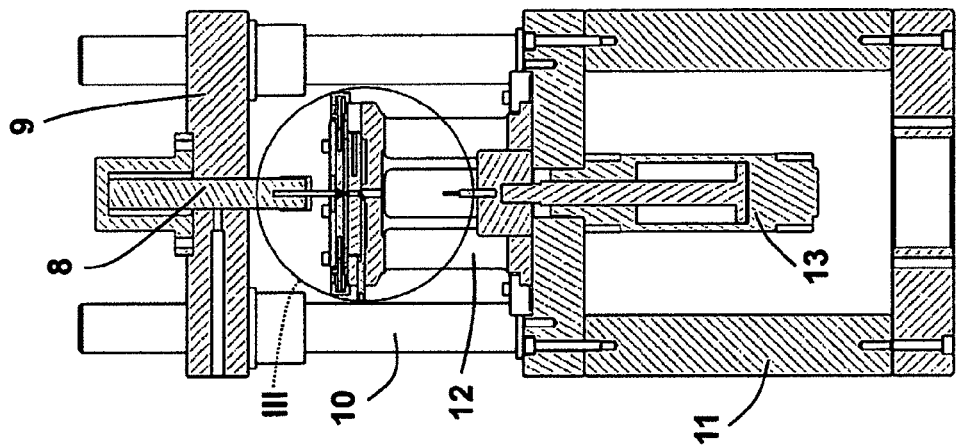
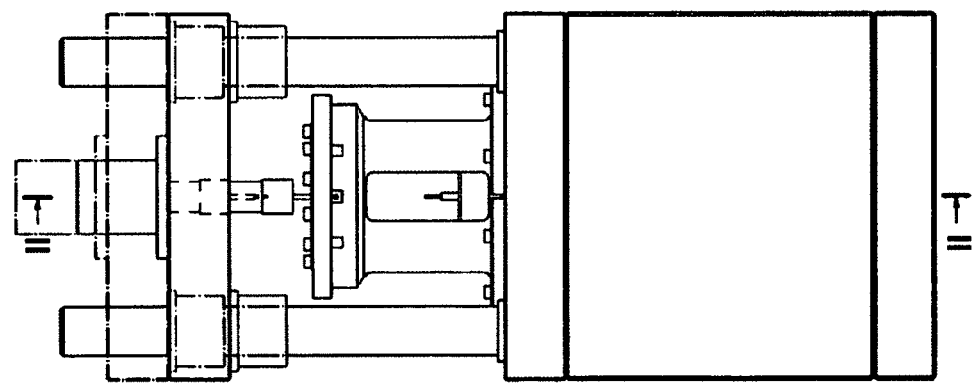

METHOD FOR PRODUCING A SMALL THIN-WALLED TUBE FROM A MAGNESIUM ALLOY

The invention relates to a method for producing a small thin-walled tube for a medical application or for a medical product, in particular for a stent, wherein a blank is shaped from an in particular bioresorbable magnesium alloy to form a small tube, after which the small tube can be used for medical purposes or the medical product, such as a stent, can be produced therefrom.

Furthermore, the invention relates to a device for producing a small thin-walled tube for medical applications or for a medical product from a blank of a magnesium alloy, comprising a male die with a base body and a mandrel tapered relative to the base body, as well as a female die with a receiving region and a contouring region, wherein the contouring region has a diameter which is larger than an outer diameter of the mandrel, and wherein the male die can be moved into the female die.

In medicine so-called stents are used in order to support blood vessels in their shape when medically necessary. A stent is produced from a small tube, e.g., by laser cutting, so that a latticed structure is obtained which can be expanded elastoplastically after insertion into a blood vessel in order to develop a supporting effect in the blood vessel.

Usually a stent is produced from stainless steel or plastic, with the disadvantage that inflammations or permanent tissue reactions can be triggered after the insertion of the stent. Furthermore, a stent can stiffen a blood vessel, whereby an impediment to elastic movements with which a blood vessel optimally transports blood through the body, can result. Postoperative measures are therefore often necessary after the insertion of a stent.

Recent studies indicate that at least certain selected magnesium alloys are suitable as stent materials and can be used in the human or animal body. Magnesium alloys successively corrode in body fluids like blood and can easily be resorbed by the body with the released quantities per time unit. That means that a stent can be provided which fulfills the required support effect over a certain period and ultimately dissolves without negative effects.

Small tubes that are produced by means of tube drawing methods are used as a semi-finished product for a production of stents. The geometric demands on the small tube are defined by tolerances with respect to wall thickness, outer diameter, concentricity and roundness, which with usual wall thicknesses of 0.1 to 1 mm and outer diameters of 2 to 20 mm range in orders of magnitude of a few 0.001 mm. The length of conventional stents is approximately in the range of 20 to 200 mm.

A production of the semi-finished product by tube drawing is very complex, since several shaping steps or drawing steps with intermediate heat treatments lasting several hours to re-establish the workability of the material are necessary until a final geometry is achieved. This is associated with high expenditure in terms of production engineering, energy and time. For example, a production process for semi-finished small tubes can take up to 60 days.

This is where the invention starts. The object of the invention is to disclose a method of the type referenced at the outset, with which small thin-walled tubes can be produced from a magnesium alloy quickly and with high production quality.

A further object of the invention lies in disclosing a device of the type referenced at the outset with which small tubes can be produced from a magnesium alloy quickly and with high production quality.

The object in terms of method is achieved when a male die with a base body and a mandrel tapered relative to the base body as well as the blank is produced with a blind hole or an opening by means of a method of the type mentioned at the outset, wherein a diameter of the blind hole or the opening of the blank is equal to or greater than an outer diameter of the mandrel, after which the blank with inserted mandrel with the male die is pressed forwards at least in part through a female die with a receiving region and a contouring region, wherein the contouring region has a diameter which is larger than the outer diameter of the mandrel, but smaller than an outer diameter of the blank, in order to form the small tube.

One advantage achieved with the invention can be seen in that a small tube is produced by solid-blank forming from a blank of a magnesium alloy so that only one process step is necessary in order to achieve a final tube geometry. Furthermore, the small tube can be produced with high production quality, in particular with respect to the dimensions of the small tube, wherein extremely small tolerances can be maintained, since the contouring region of the female die and the outer diameter of the mandrel determine the outer diameter of the small tube or the inner diameter thereof. A stent can be easily produced from a small tube produced according to the invention, for example, by laser cutting.

To carry out the method according to the invention, it is sufficient that the blank is embodied with a blind hole. However, it is more expedient for the blank to be provided with an opening, the diameter of which corresponds to the diameter of the mandrel or is slightly larger than this so that the mandrel can be guided through the opening.

The outer diameter of the blank is preferably selected according to a free diameter of the receiving region so that during the pressing of the blank the same bears in the receiving region, and material of the blank is pressed exclusively into a free region between the contouring region and the mandrel. It has proven to be expedient thereby that the blank is used in cylindrical shape, since the receiving region generally is likewise embodied in a cylindrical manner.

In order to keep press forces as low as possible and to achieve a shaping in a simple manner, it is preferred that the blank is pressed through the female die in the heated state and/or with heating. In this regard it has proven to be expedient for most magnesium alloys for the blank to be pressed through the female die at a temperature in the range of 200° C. to 450° C. At temperatures of less than 200° C., high press forces can be necessary. At temperatures of more than 450° C. a magnesium alloy can be so soft that a processing is likewise rendered difficult. However, in individual cases, depending on the alloy system, higher temperatures can also be provided, as long as a sufficient distance is maintained from the melting point or melting interval.

In particular when the blank is pressed through the female die in the heated state or a heating is to take place during pressing, it is expedient that the female die and/or the male die are heated.

It is particularly preferred for the blank to be formed from an extruded magnesium alloy. Although in principle a cast material can be used directly, inhomogeneities can then occur in the small tube, which are attributable to the casting. This can be disadvantageous in particular when a stent is produced from the small tube by laser cutting or in another manner, the fine lattice of which in the presence of inhomogeneities in the thin webs is less loadable, which has proven to be disadvantageous in particular during the expansion of the stent in a blood vessel. However, if the blank is extruded, higher quality stents can be produced, since a grain refinement and a homogenization of the structure occur during an extrusion so that an optimal starting material is already present, which can then be pressed again, wherein a further grain refinement and homogenization of the structure occur. Furthermore, the mechanical properties as well as the corrosion resistance can be improved thereby. A heat treatment of the small tube produced in this manner can thus sometimes even be omitted, depending on the processed alloy.

The method according to the invention has proven useful in particular for small tubes with small outer diameters and a small wall thickness. It is preferred that the blank with an outer diameter of no more than 10 mm is used and the small tube with an outer diameter of less than 3 mm, preferably less than 2.5 mm, and a wall thickness of less than 0.5 mm, preferably less than 0.35 mm, in particular 70 to 300 µm, is produced.

In order to be able to produce several identical small tubes in a short time, it is expedient that an extrusion butt adhering to the male die is drawn off by means of a scraper during the retraction of the male die into a starting position. For the same reason it can also be provided that an extrusion butt is ejected from the female die after the male die is retracted.

The further object of the invention is attained in that with a device of the type mentioned at the outset a first transition from the base body to the mandrel is embodied as a concave arc with a length of no more than 10 mm or as a chamfer with such a length and an angle of no more than 160° C., a second transition from the receiving region to the contouring region of the female die is embodied as a convex arc with a length of no more than 10 mm or as a chamfer with such a length and an angle of no more than 160°, an outer diameter of the mandrel is no more than 1 mm smaller than a free diameter of the contouring region and an outer diameter of the base body corresponds to a free diameter of the receiving region.

One advantage achieved with a device according to the invention is to be seen in that press forces can be kept low due to the provided geometric embodiment of the transitions from the base body to the mandrel of the male die and from the receiving region to the contouring region of the female die, which promotes a rapid shaping of a blank. Furthermore, small thin-walled tubes with high production quality can be produced.

It is preferred that the first transition is embodied as a concave arc with a length of no more than 2 mm, preferably 1.5 mm, or as a chamfer with such a length and an angle of no more than 160°, preferably no more than 130°, and the second transition is embodied as a convex arc with a length of no more than 2 mm or as a chamfer with such a length and an angle of no more than 160°, preferably no more than 130°.

Preferably, with a device according to the invention, one or more heating devices are provided for the male die and/or the female die.

Figure 5:
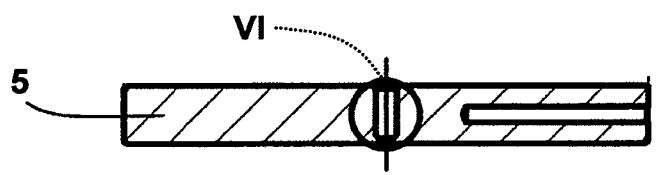
Figure 6:
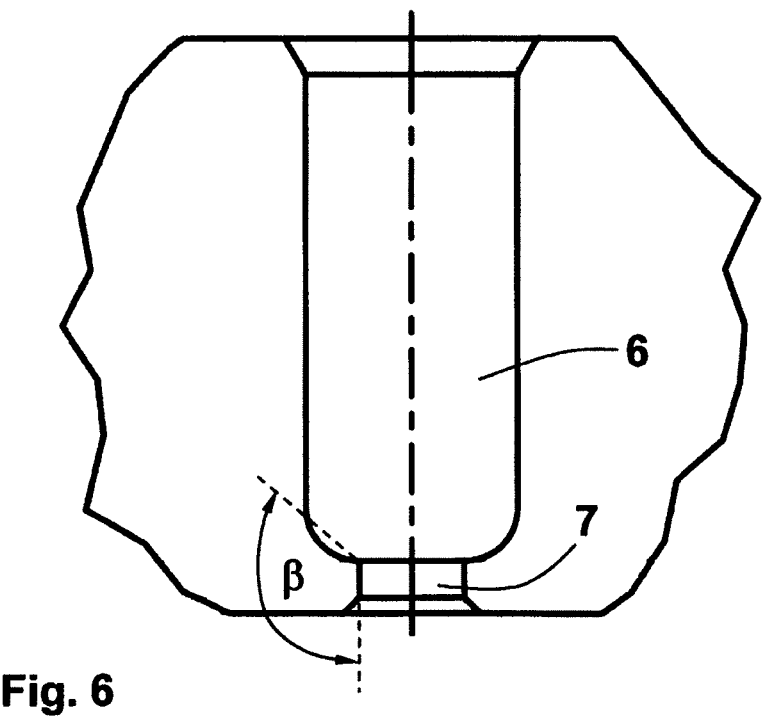
Figure 7:
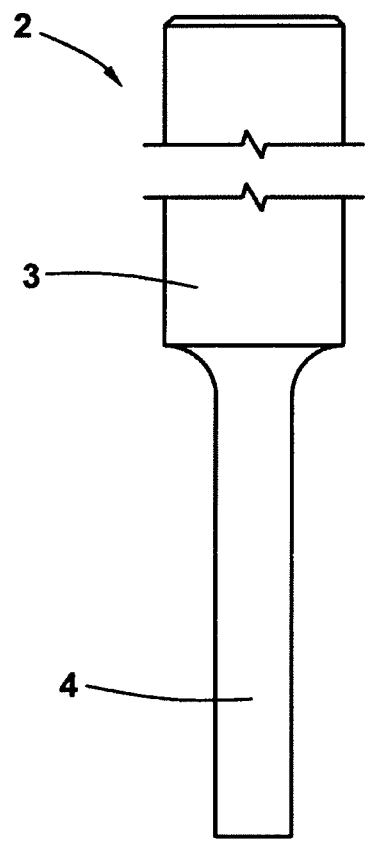
Figure 8:
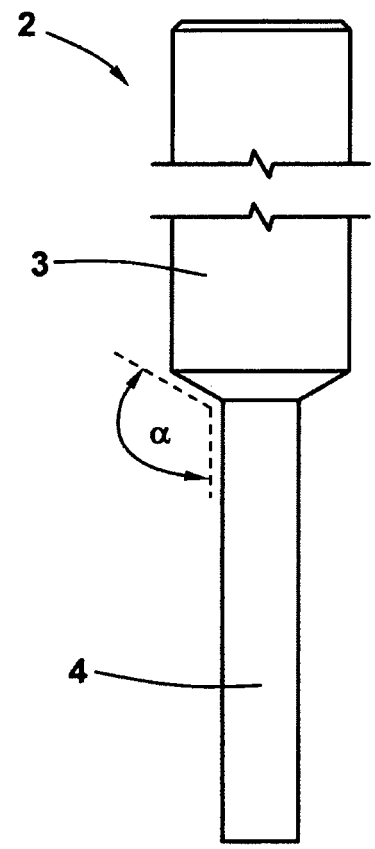
Figure 9A:
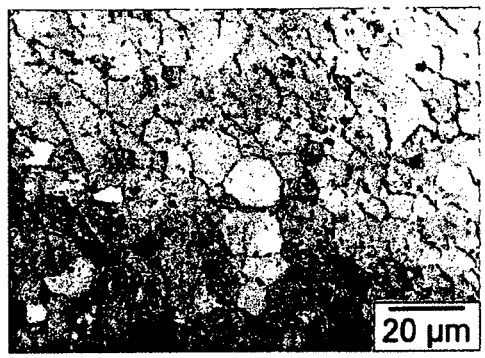
Figure 9B:
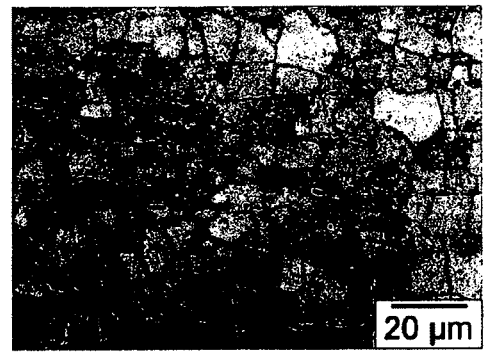
Figure 10A:
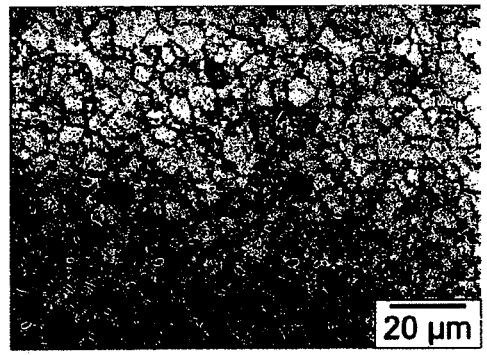
Figure 10B:
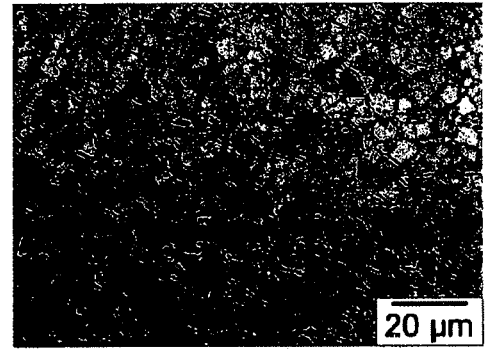

Further features, advantages and effects of the invention are shown by the following description of an exemplary embodiment. The drawings, to which reference is made thereby, show:

FIG. 1 a device according to the invention in a front view;
FIG. 2 a cross section according to the line II-II in FIG. 1;
FIG. 3 an enlarged cross section according to the circle III in FIG. 2;
FIG. 4 a female die in plan view;
FIG. 5 a cross section through a female die according to FIG. 4;
FIG. 6 an enlarged section according to the circle VI in FIG. 5;
FIG. 7 a male die with an arc;
FIG. 8 a male die with a chamfer;
FIG. 9a a cross section of an extruded bolt;
FIG. 9b a longitudinal section of an extruded bolt;
FIG. 10a a cross section of a small tube according to the invention;
FIG. 10b a longitudinal section of a small tube according to the invention.

FIGS. 1 through 3 show a device 1 with which small thin-walled tubes can be produced from a magnesium alloy. The device 1 comprises a male die 2 with a base body 3 and a mandrel 4. The mandrel 4 is embodied in a solid manner and fixedly connected to the base body 3, although the mandrel 4 can also be slidably supported with respect to the base body 3. In the region of an end of the base body 3, the male die 2 is attached in a holder 8. In turn the holder 8 is arranged in a horizontal profile 9, which profile 9 is slidably supported on several guides 10, so that the holder 8 and thus also the male die 2 can be moved vertically into a female die 5.

The guides 10 and the female die 5 are arranged on a base 11, wherein the female die 5 is held spaced apart from the base 11 with guide rails 12. The guide rails 12 are used not only to space the female die 5 apart from the base 11, but at the same time as a guide for a device 13, which can be moved vertically and with the tip of which, which has the same dimensions as the mandrel 4, extrusion butts can be ejected from the female die 5.

As can be seen from FIG. 3, a scraper disk 14 with a central opening is arranged above the female die 5. A diameter of the central opening corresponds to an outer diameter of the base body 3. It can thus be ensured that extrusion butts possibly adhering to the male die 2 are scraped off during retraction into a starting position of the same. Below the female die 5 a shearing device 15 is provided that can be displaced horizontally within limits, with which device a produced small tube can be separated from the rest of a blank or extrusion butt.

The female die 5 is shown in greater detail in FIGS. 4 through 6. The female die 5 is embodied in a circular manner and can have a diameter of up to 300 mm. The female die 5 is equipped with several heating cartridges 16, with which the female die 5 can be heated. Furthermore, a thread 17, merely indicated, is provided, in which an adjusting bolt engages, so that an opening of the female die 5 with respect to a vertical axis, along which the male die 2 or a tip of the device 13 moves, can be optimally adjusted. A receiving region 6 and a contouring region 7 are provided in the region of the opening of the female die 5. The receiving region 6 has a free diameter, which corresponds to the outer diameter of the base body 3. The receiving region 6 merges in the region of its lower end via a convex arc into the contouring region 7. The arc typically has a length of less than 10 mm and alternatively can also be replaced by a chamfer of corresponding length, wherein then an angle β is no more than 160°. The contouring region 7 has a free diameter, which is no more than 1 mm larger than an outer diameter of the mandrel 4 so that in particular small thin-walled tubes can be produced.

In FIGS. 7 and 8 various embodiments of the male die 2 are shown, which interacts with the female die 5 in the production of a small tube. In the variant according to FIG. 7, a transition from the base body 3 to the mandrel 4 is embodied as a concave arc, the length of which is less than 10 mm. According to FIG. 8, the concave arc can also be replaced by a chamfer of corresponding length, wherein an angle α is no more than 160°.

To produce a small thin-walled tube from a magnesium alloy, in particular a magnesium forgeable alloy, firstly a cylindrical bolt is produced by means of extrusion, the outer diameter of which corresponds to a free diameter of the receiving region 6, and a blank is cut to length. Subsequently, a central opening is made in the blank, for example by drilling. Thereafter the blank is placed in the receiving region 6 of the female die 5. Alternatively, it is also possible to place the blank on the mandrel 4 of the male die 2. Finally, the male die 2 is moved downwards in the representation according to FIG. 2, that is, into the female die 5. A press force is thereby applied to the blank in the region of the transition from the base body 3 to the mandrel 4. Since an outer diameter of the blank corresponds to a free diameter of the receiving region 6, the blank can be deformed only forwards in the direction of the contouring region 7, wherein a free diameter of the contouring region 7 defines an outer shape of the produced small tube, whereas the mandrel 4 establishes a free inner cross section of the small tube. The press forces are overall relatively low with a device according to the invention, which is attributable to the provided transitions and a good introduction of force into the blank. It is also expedient in most cases to heat the blank before and/or during the deformation, in order to facilitate a flow of the material. Typical temperature regions for magnesium alloys are in the range of 200° C. to 450° C. However, in principle it is also conceivable to deform the blank by cold working and to subject the small tube produced in this manner subsequently to a heat treatment or to passively ensure a heating by means of a sufficiently large deformation speed and a deformation heat associated therewith.

Naturally, in practice with a series production several devices 1 can run parallel next to one another in order to achieve high production runs of small tubes in a short time.

FIG. 9a shows a transverse section of an extruded bolt of a magnesium alloy, from which blanks are removed to produce small tubes. FIG. 9b shows a corresponding longitudinal section. As can be seen from FIGS. 9a and 9b, the structure of the bolt is largely homogeneous and has an average grain size of much less than 20 μm.

FIGS. 10a and 10b show a transverse section and a longitudinal section of a small tube, which was produced from a blank with a starting structure according to FIG. 9a or 9b. As can be seen, the deformation of the blank to form the small tube led to a further homogenization of the structure and to a grain refinement, which is favorable with respect to mechanical properties, in particular when a stent is produced from the small tube, which is composed only of thin webs connected to one another, which furthermore must withstand stress during an expansion of the stent.

Through an adjustment of the grain size of the structure a corrosion behavior of the small tubes or stents made therefrom can also be adjusted so that it is possible to produce stents with a predetermined service life in the human or animal body.

The invention claimed is:

1. A method for producing a small thin-walled tube for a medical application or for a medical product, the method comprising:
    shaping an extruded magnesium alloy blank to form a small tube, whereby the small tube is usable for medical purposes or the medical product,
    wherein a male die comprises a base body and a mandrel tapered relative to the base body and the blank comprises one of a blind hole or an opening having a diameter that is equal to or greater than an outer diameter of the mandrel,
    the shaping comprising inserting the mandrel into the one of the blind hole or opening of the blank and then pressing the blank forward at least in part through a female die comprising a receiving region and a contouring region having a diameter that is larger than the outer diameter of the mandrel, but smaller than an outer diameter of the blank, in order to form the small tube.

2. The method according to claim 1, further comprising selecting the outer diameter of the blank according to a diameter of the receiving region.

3. The method according to claim 2, wherein the blank has a cylindrical shape.

4. The method according to claim 1, further comprising pressing the blank through the female die at least one of in a heated state and/or with heating.

5. The method according to claim 4, wherein the blank is pressed through the female die at a temperature in a range of 200° C. to 450° C.

6. The method according to claim 1, further comprising at least one of heating the female die and/or the male die.

7. The method according to claim 1, wherein the blank has an outer diameter of no more than 10 mm and the produced small tube has an outer diameter of less than 3 mm and a wall thickness of less than 0.5 mm.

8. The method according to claim 1, further comprising drawing off an extrusion butt adhering to the male die with a scraper during a retraction of the male die into a starting position.

9. The method according to claim 8, wherein, after the male die is retracted, the method further comprises ejecting the extrusion butt from the female die.

10. The method according to claim 7, wherein the outer diameter of the produced small tube is less than 2.5 mm.

11. The method according to claim 7, wherein the wall thickness of the produced small tube is less than 0.5 mm.

12. The method according to claim 7, wherein the wall thickness of the produced small tube is between 70 to 300 μm.

13. The method according to claim 1, further comprising forming a stent from the small tube.

14. The method according to claim 1, wherein the extruded magnesium alloy blank is a biosorbable extruded magnesium alloy blank.

* * * * *